United States Patent [19]

Lok et al.

[11] Patent Number: 4,948,721

[45] Date of Patent: Aug. 14, 1990

[54] PHOTOGRAPHIC RECORDING MATERIALS WITH ENHANCED LATENT IMAGE STABILITY

[75] Inventors: Roger Lok, Hilton; Ronald E. Leone, Rochester, both of N.Y.

[73] Assignee: Eastman Kodak Company, Rochester, N.Y.

[21] Appl. No.: 385,044

[22] Filed: Jul. 26, 1989

[51] Int. Cl.$^5$ ................................................ G03C 1/02
[52] U.S. Cl. .................................... 430/551; 430/614; 430/610
[58] Field of Search ........................ 430/614, 551, 610

[56] References Cited

U.S. PATENT DOCUMENTS

| 3,954,478 | 5/1976 | Arai et al. | 430/551 |
| 4,297,441 | 10/1981 | Kaneko et al. | 430/551 |
| 4,374,196 | 2/1983 | Herz | 430/505 |
| 4,423,140 | 12/1983 | Herz | 430/445 |
| 4,780,400 | 10/1988 | Beltramini et al. | 430/505 |

FOREIGN PATENT DOCUMENTS

| 107574 | 6/1939 | Australia | 430/614 |
| 0250740 | 4/1987 | European Pat. Off. | |

Primary Examiner—Paul R. Michl
Assistant Examiner—Thomas R. Neville
Attorney, Agent, or Firm—Paul A. Leipold

[57] ABSTRACT

Latent image stability is enhanced in photographic recording materials using N-alkyl- or N-alkenylbenzothiazolium or -benzoselenazolium salts.

16 Claims, No Drawings

PHOTOGRAPHIC RECORDING MATERIALS WITH ENHANCED LATENT IMAGE STABILITY

The present invention relates to photographic recording materials and more particularly to photographic recording materials having enhanced latent image keeping stability.

A visible image is formed in silver halide photographic materials by exposure of the material to actinic radiation to form a record of the exposure. This record, which is invisible to the unaided eye, yields a visible image by photographic processing of the exposed material.

It is generally believed that the latent image comprises minute specks of metallic silver. These specks form in or on individual silver halide grains by interaction between silver ions and photoelectrons generated by absorption of actinic radiation by the silver halide grains.

Processing of most common silver halide photographic materials includes a development step in which the material is contacted with an aqueous alkaline solution of a developing agent. The developing agent, which is a reducing agent, selectively reduces to metallic silver those silver halide grains containing a latent image.

It is recognized in the photographic art that a latent image is not permanent and that, with passage of time, silver halide grains which would be developable immediately after exposure become nondevelopable. This phenomenon is termed latent image fading and manifests itself as a loss in image density in the developed image and a consequent loss in speed in the silver halide photographic material.

If silver halide materials were developed immediately following imagewise exposure, latent image fading would not be a problem. However, with many silver halide materials, delays between exposure and processing frequently occur. For example, with amateur film materials in which multiple images are formed on a single roll of film there is often a delay of months between the time the first image is exposed and the time the exposed material is processed. With such materials latent image fading can present a significant problem and compounds are added to photographic materials to prevent or reduce this undesirable effect. These compounds are referred to as latent image stabilizers and prevention or reduction of latent image fading is referred to as latent image stabilization.

Various attempts have been made to solve this problem. One attempt is mentioned in U.S. Pat. No. 3,954,478 where N-2-propenyl-benzothiazolium and N-2-propenyl-naphthothiazolium salts are described as being useful for this purpose.

Other proposed solutions to latent image instability are described in U.S. Pat. No. 4,374,196 where acyclic compounds, obtained by basic hydrolysis of N-alkenylthiazolium salts, are shown to reduce latent image instability. In U.S. Pat. No. 4,423,140 certain aromatic mercaptide compounds are described as being useful in reducing latent image instability. Published European Application 250,740 discloses 2-unsubstituted N-alkenylthiazolium salts as latent image stabilizers.

Notwithstanding these earlier attempts to reduce or to eliminate latent image instability, the need still exists in the photographic art for more effective stabilizers for latent images in exposed silver halide recording materials.

The present invention satisfies this need by providing a photographic recording material comprising a support and a silver halide emulsion which has associated therewith an N-alkyl or N-alkenylbenzothiazolium or benzoselenazolium salt having the structural formula:

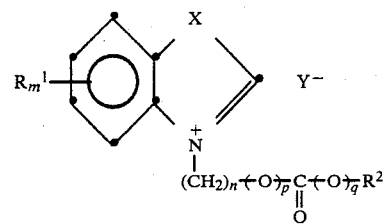

wherein:

X is sulfur or selenium;
$R^1$ is hydrogen, halogen, lower alkyl or lower alkoxy;
$R^2$ is $-CH_2-CH_3$, $-CH=CH_2$ or $-CH_2CH=CH_2$;
Y is a counterbalancing ion;
m is 0 to 4;
n is 1 to 5; and
p and q are each 0 or 1, with the proviso that when p is 1, q is 0 and when q is 1, p is 0.

When $R^1$ is alkyl or alkoxy, the length of the carbon chain which designates "lower" is from 1 to about 5 carbon atoms, preferably from 1 to about 3 carbon atoms. The alkyl or alkoxy group can be straight or branched chain. When $R^1$ is halogen it is preferably chloro.

The counterbalancing ion Y can be any anion compatible with the photographic material in which it is coated. Useful ions include inorganic anions such as halides, halophosphates, trifluoromethanesulfonates and the like.

While n can be an integer as high as 5, the preferred value is from 1 to 3. The carbon chain can be straight or branched chain, such as for example n-propyl, s-butyl or t-amyl.

The proviso that only one of p or q be 1 is to assure that only one oxygen atom is adjacent the carbonyl group in the substituent bonded to the ring nitrogen atom. The oxygen atom can be located between the alkylene chain and the carbonyl group or between the carbonyl group and the terminal ethyl or allyl group.

Specific compounds falling within this invention which can provide improved latent image stability in an exposed photographic silver halide emulsion include the following:

1.

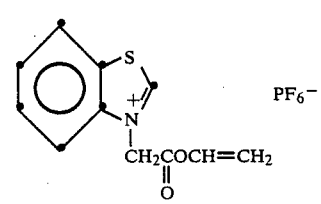

-continued
2. 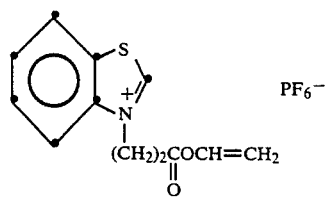 PF$_6^-$
3. 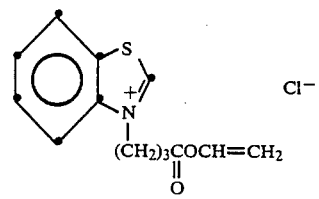 Cl$^-$
4. 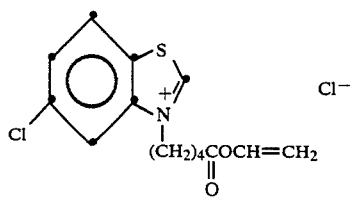 Cl$^-$
5. 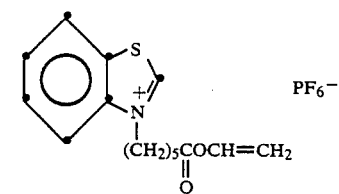 PF$_6^-$
6. 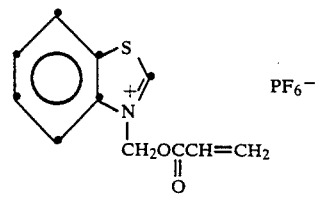 PF$_6^-$
7. 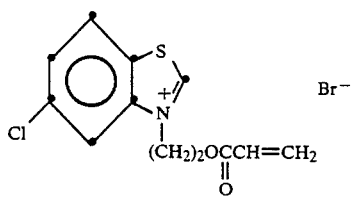 Br$^-$
8. 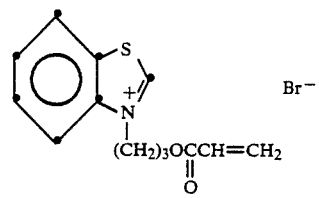 Br$^-$
9. 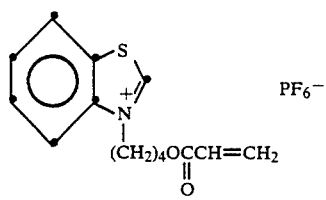 PF$_6^-$
-continued
10. 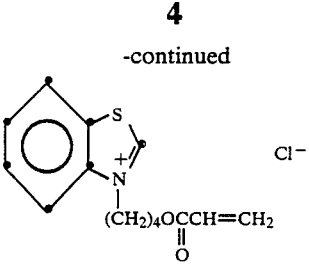 Cl$^-$
11. 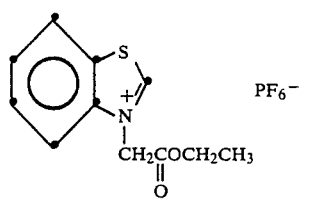 PF$_6^-$
12. 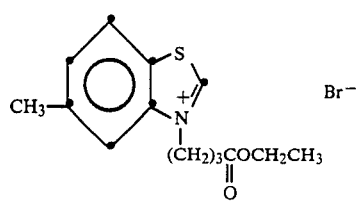 Br$^-$
13. 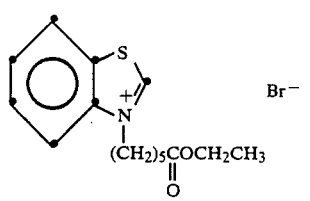 Br$^-$
14. 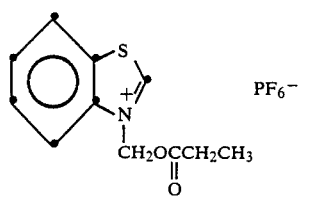 PF$_6^-$
15. 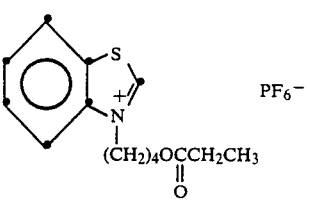 PF$_6^-$
16. 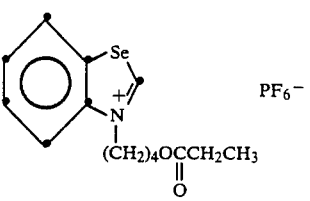 PF$_6^-$
17. 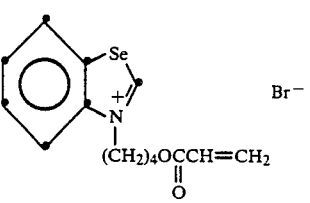 Br$^-$

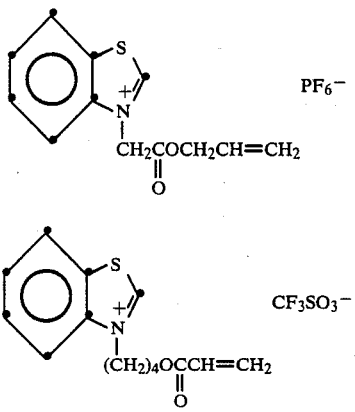

18.

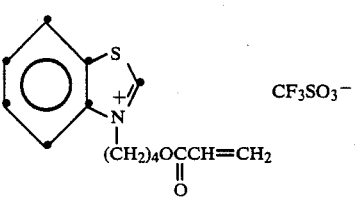

19.

Compounds useful in this invention can be prepared for example by treating an alcohol with trifluoromethanesulfonic anhydride in the presence of pyridine and subsequently treating the product with a benzothiazole or a benzoselenazole under a nitrogen environment to produce the desired salt.

Details of such preparation are illustrated by the following syntheses:

EXAMPLE 1

Preparation of Compound No. 19

In a flask equipped with a magnetic stirrer, dropping funnel, nitrogen inlet, and reflux condenser were placed pyridine (0.79 g., 0.01 mole) and dichloromethane (20 ml). The flask was chilled to $-40°$ in a dry ice-acetonitrile bath and a nitrogen atmosphere was maintained inside. Trifluoromethanesulfonic anhydride (2.82 g., 0.01 mole) in dichloromethane (20 ml) was added dropwise. The resulting thick mixture was stirred for 10 minutes at $-40°$. 1,4-Butane-diol monoacrylate (1.44 g., 0.01 mole) in dichloromethane (20 ml) was added dropwise over 30 minutes. The mixture was stirred at $-40°$ for 10 more minutes. This mixture was filtered while still cold through a fritted glass funnel directly into another reaction flask containing benzothiazole (1.10 g, 0.008 mole) and dichloromethane (40 ml). This flask was chilled in an ice bath and a nitrogen atmosphere was maintained inside. The mixture was stirred at ice bath temperature for 2 hours and then at room temperature for 20 hours. A white solid separated from solution. The mixture was filtered and the collected solid was washed with fresh dichloromethane. The material was dried overnight at room temperature in a vacuum oven. This gave 1.50 g of a white powder. The solvent was removed from the above filtrate. The remaining solid residue was stirred and crushed under water. This mixture was filtered and the collected solid was washed first with water and then with diethyl ether. This material was dried overnight at room temperature in a vacuum oven. This gave 1.22 g of a second crystalline crop of the product. Total yield 2.72 g (83%) of a white powder, m.p. 138°-141°.

Anal. Calcd. for: $C_{15}H_{16}F_3NO_5S_2 + 0.5\ H_2O$: C, 42.9; H, 4.0; N, 3.3; S, 15.2. Found: C, 43.1; H, 3.8; N, 3.3; S, 14.8.

EXAMPLE 2

Preparation of Compound No. 15

1,4-Butanediol monoacrylate (4.32 g, 0.03 mole), platinum oxide (8%, 0.10 g), and ethyl acetate (100 ml) were placed in a Parr hydrogenation bottle. This mixture was placed on a Parr apparatus and was hydrogenated at room temperature until hydrogen uptake ceased. The reaction took about 2 hours to complete. The mixture was filtered to remove the catalyst. The solvent was removed from the filtrate on a rotary evaporator. This gave 4.3 g (98%) of 4-hydroxylbutyl propionate as a clear oil. An nmr spectrum verified the structure of the product.

In a flask equipped with a magnetic stirrer, dropping funnel, nitrogen inlet and reflux condenser were placed pyridine (0.79 g, 0.01 mole) and dichloromethane (20 ml). The flask was chilled in an ice-salt bath to 0° and a nitrogen atmosphere was maintained inside. Trifluoromethanesulfonic anhydride (2.82 g, 0.01 mole) in dichloromethane (20 ml) was added dropwise and a white precipitate formed. The mixture was stirred for 10 minutes at 0°. A solution of 4-hydroxylbutyl propionate (1.46 g, 0.01 mole) in dichloromethane (20 ml) was added dropwise over 20 minutes. The mixture was stirred at 0° for 15 more minutes. The mixture was then filtered while still cold through a pad of sodium sulfate. The filtrate was quickly added to another reaction flask containing benzothiazole (1.10 g, 0.008 mole) and dichloromethane (40 ml). The resulting solution was stirred at room temperature under a nitrogen atmosphere for 17 hours. The solvent was removed on a rotary evaporator to give a tan oil. This oil was stirred with water (40 ml) for 15 minutes. The aqueous mixture was shaken with diethyl ether to remove neutral material. The aqueous layer was transferred to a beaker. Potassium hexafluorophosphate (1.2 g) was added with stirring. The aqueous mixture was stirred for 30 minutes at room temperature and then was filtered. The collected solid was washed first with water, and then with diethyl ether. The product was dried overnight at 45° in a vacuum oven. This gave 1.0 g (31%) of a pink tinted white powder, m.p. 124°-127°.

Anal. Calcd. for: $C_{14}H_{18}F_6NO_2PS$: C, 41.1; H, 4.4; N, 3.4; S, 7.5. Found: C, 41.4; H, 4.5; N, 3.8; S, 7.5.

EXAMPLE 3

Preparation of Compound No. 1

Vinyl bromoacetate (1.65 g, 0.01 mole) and benzothiazole (1.35, 0.01 mole) were mixed together in a round-bottom flask. The resulting solution was stirred and heated to 80°-85° (oil bath temperature) for 2 hours.

The mixture solidified and was allowed to stand overnight at room temperature. The solid material was stirred with diethyl ether. The mixture was filtered and the collected solid was washed with fresh diethyl ether. The material was allowed to air dry at room temperature. It was then dissolved in water (35 ml). The aqueous solution was stirred at room temperature and potassium hexafluorophosphate (1.2 g) was added in portions. A precipitate formed. The mixture was stirred for ½ hour and was then filtered. The collected solid was washed first with water and then with diethyl ether. The product was dried for 5 hours at 45° in a vacuum oven. This gave 1.43 g (39%) of a beige colored powder, m.p. 172°-174.

Anal. Calcd. for: $C_{11}H_{10}F_6NO_2PS$: C, 36.2; H, 2.8; N, 3.8; S, 8.8. Found: C, 36.4; H, 2.8; N, 3.8; S, 8.8.

EXAMPLE 4

Preparation of Compound No. 11

In a flask equipped with a magnetic stirrer, dropping funnel, nitrogen inlet and a reflux condenser were placed pyridine (0.79 g, 0.01 mole) and dichloromethane (20 ml). The flask was chilled to 0° in an ice-salt bath and a nitrogen atmosphere was maintained inside. A solution of trifluoromethanesulfonic anhydride (2.82 g, 0.01 mole) in dichloromethane (20 ml) was added dropwise. The resulting thick suspension was stirred for 10 more minutes at 0°. A solution of ethyl glycolate (1.04 g, 0.01 mole) in dichloromethane (20 ml) was added dropwise over 20 minutes.

After the addition was complete the mixture was stirred for 10 more minutes at 0°. The cold mixture was filtered through a pad of sodium sulfate. The filtrate was immediately added to a solution of benzothiazole (1.10 g, 0.008 mole) in dichloromethane (50 mL). The resulting solution was stirred at room temperature under a nitrogen atmosphere for 17 hours. The solvent was removed on a rotary evaporator to give an oil. This oil was stirred with warm water (40 ml). The aqueous mixture was shaken with diethyl ether. The aqueous layer was separated into a beaker. The solution was stirred at room temperature and potassium hexafluorophosphate (1.4 g) was added. A white precipitate formed. This mixture was stirred for 30 minutes and was then filtered. The collected solid was washed first with water, and then with diethyl ether. The product was dried at 40° for several hours in a vacuum oven. The crude product was recrystallized from ethanol (35 ml). The mixture was filtered and the recrystallized product was washed with pentane. It was dried in a vacuum oven at 40° for several hours. This gave 0.95 g (32%) of a white solid, m.p. 137°–139°.

Anal. Calcd. for: $C_{11}H_{12}F_6NO_2PS$: C, 36.0; H, 3.3; N, 3.8; S, 8.7. Found: C, 36.0; H, 3.3; N, 3.8; S, 8.8.

EXAMPLE 5

Preparation of Compound No. 18

Allyl chloroacetate (1.35 g, 0.01 mole) and benzothiazole (1.35 g, 0.01 mole) were mixed together in a round-bottom flask. The resulting solution was stirred and heated to 100°–105° (oil bath temperature) for 8 hours. The dark viscous mixture was stirred with water and ether. The aqueous layer was separated off and the ether layer was discarded. The aqueous layer was filtered and the resulting solution was stirred at room temperature. Potassium hexafluorophosphate (1.0 g) was added and the mixture was stirred for 30 minutes. A precipitate was obtained. The mixture was filtered and the collected solid was washed first with water, then with diethyl ether. The product was allowed to air dry at room temperature. This gave 0.20 g (5%) of an orange powder, m.p. 128°–130° (dec.).

Anal. Calcd. for: $C_{12}H_{12}F_6NO_2PS$: C, 38.0; H, 3.2; N, 3.7; S, 8.5. Found: C, 38.8; H, 3.3; N, 3.8; S, 7.7.

The benzothiazolium and benzoselenazolium salts described herein can be added to a silver halide emulsion at any point subsequent to precipitation of the silver halide grains. Preferably, the salts are added to an emulsion after chemical and spectral sensitization, but prior to coating. However, the salts can be present during these sensitization procedures.

The optimum amount of benzothiazolium or benzoselenazolium salt added to an emulsion will depend upon various factors such as the particular salt employed, the particular silver halide emulsion used or the nature of other components of the emulsion. Useful amounts are within the range of from about 0.002 to about 10 millimoles of salt per mole of silver. Preferably, the salt is incorporated in the emulsion in an amount of from about 0.02 to about 0.5 millimole per mole of silver.

The silver halide emulsions employed in the present invention can be any of the silver halide emulsions known in the art which are desirably protected against latent image instability or fading. The silver halide emulsions can be comprised of silver bromide, silver chloride, silver chlorobromide, silver chloroiodide, silver bromoiodide, silver chlorobromoiodide or mixtures thereof. The emulsions can include coarse, medium or fine grains and can be monodisperse or polydisperse.

The silver halide emulsions are preferably surface latent image-forming emulsions. They can be chemically sensitized as illustrated by T. H. James, The Theory of the Photographic Process, 4th Ed., MacMillan, 1977, pp. 67–76, or with sulfur, selenium, tellurium, gold, platinum, palladium, iridium, osmium, rhenium or phosphorus sensitizers, or combinations of these sensitizers, as illustrated by Research Disclosure, Vol. 134, Jun. 1975, Item 13452, or in U.S. Pat. Nos. 1,623,499; 1,673,522; 2,399,083; 2,642,361; 3,297,447; 3,297,446; 1,315,755; 3,772,031; 3,761,267; 3,857,711; 3,565,633; 3,901,714 and 3,904,415 and U.K. Patent No. 1,396,696.

Chemical sensitization can optionally be conducted in the presence of thiocyanate derivatives, as described in U.S. Pat. Nos. 2,222,264 and 2,642,361; thioether compounds, as disclosed in U.S. Pat. Nos. 2,521,926; 3,021,215 and 4,054,457; or azaindenes, azapyridazines and azapyrimidines, as described in U.S. Pat. Nos. 3,411,914; 3,554,757; 3,565,631 and 3,901,714. Additionally or alternatively, the emulsions can be reduction sensitized e.g., with hydrogen, as illustrated by U.S. Pat. Nos. 3,891,446 and 3,984,249 by low pAg (e.g., less than 5), high pH (e.g., greater than 8) treatment or through the use of reducing agents, such as stannous chloride, thiourea diozide, polyamines and amineboranes, as illustrated by Research Disclosure, Vol. 136, Aug. 1975, Item 13654, or U.S. Pat. Nos. 2,518,696; 2,739,060; 2,743,182; 2,743,183; 2,983,609; 3,026,203 and 3,361,564 (Research Disclosure is published by Industrial Opportunities Ltd., Homewell, Havant Hampshire, PO9 1EF, United Kingdom.)

The silver halide emulsions can be spectrally sensitized with dyes from a variety of classes, including the polymethine dye class, which includes the cyanines, merocyanines, complex cyanines and merocyanines (i.e., tri-, tetra-, and poly-nuclear cyanines and merocyanines), oxonols, hemioxonols, styryls, merostyryls and streptocyanines. Particularly useful dyes are benzoxazole, benzimidazole and benzothiazole carbocyanine dyes.

The photographic silver halide emulsions can contain various colloids alone or in combination as vehicles. Suitable hydrophilic materials as well as hardeners therefore, are described in Research Disclosure, Dec. 1978, Item 17643, Sections IX and X.

The photographic silver halide emulsions and elements employing the stabilizing agents of this invention can contain other addenda conventional in the photographic art. Useful addenda are described, for example, in Research Disclosure, Dec. 1978, Item 17643 and include antifoggants, couplers (such as dye forming couplers, masking couplers and DIR couplers) DIR compounds, anti-stain agents, image dye stabilizers, absorbing materials such as filter dyes and UV absorbers, light scattering materials, coating aids, plasticizers and lubricants.

The photographic recording materials described herein can be black-and-white or monochrome materials or they can be multilayer and/or multicolor elements comprising a support bearing one or more layers of a silver halide emulsion. These materials can be designed for processing in conventional developer solutions. Multicolor elements can contain dye image forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsion or emulsions can be disposed as one or more segmented layers.

A preferred color photographic recording material according to this invention comprises a support bearing at least one blue-sensitive silver halide emulsion layer having associated therewith a yellow dye-forming coupler, at least one green-sensitive silver halide emulsion layer having associated therewith a magenta dye-forming coupler and at least one red-sensitive silver halide emulsion layer having associated therewith a cyan dye-forming coupler, at least one of the silver halide emulsion layers containing a latent image stabilizing compound of this invention. In accordance with a particularly preferred aspect of the present invention, the stabilizing compound is contained in a yellow dye-forming blue-sensitive silver halide emulsion.

The photographic recording materials of the present invention can contain additional layers conventional in photographic elements, such as overcoat layers, spacer layers, filter layers, antihalation layers, scavenger layers and the like. The support can be any suitable support used with photographic elements. Typical supports include polymeric films, paper (including polymer-coated paper), glass and the like. Details regarding supports and other layers of the photographic elements of this invention are contained in Research Disclosure, Dec. 1978, Item 17643, referred to above.

As used herein, the term "associated therewith" signifies that the stabilizing compound is in a silver halide emulsion layer or in an adjacent layer so that the materials contained therein are accessible to one another.

The following examples further illustrate this invention.

EXAMPLE 6

Photographic Evaluations

Benzothiazolium salts as latent image keeping agents, were evaluated in a black-and-white test. This test used sulfur and gold sensitized 0.8 μm octahedral silver bromide emulsion prepared in the presence of 1,10-dithia-18-crown-6 ether and bis(2-amino-5-iodopyridine-dihydroiodide) mercuric iodide. This emulsion was coated in a single layer format. The melt pH was 5.6 and the pAg was 8.5. All the benzothiazolium salts were coated at 0.2 mmole/mole Ag. The latent imate keeping (LIK) coatings were exposed for 1/50 sec and were then incubated at 49° C./50% RH for two weeks. The raw stock keeping (RSK) coatings were incubated first, followed by exposure as described above. Both coatings were processed for 6 minutes in KODAK Rapid X-ray Developer.

The data obtained are given below in Table I. In this Table, speed values are given for fresh, raw stock keeping (RSK) and for latent image keeping (LIK). The LIK-RSK difference represents the speed loss due to latent image degradation.

TABLE I

| Compound | Fresh Speed | RSK | 2 Week Speed LIK | LIK-RSK |
|---|---|---|---|---|
| control | 255 | 269 | 187 | −82 |
| 19 | 263 | 258 | 242 | −16 |
| 15 | 264 | 261 | 243 | −18 |
| 1 | 268 | 264 | 269 | 5 |
| 11 | 253 | 250 | 226 | −24 |

From the data contained in Table I it is apparent that, in the presence of benzothiazolium salts as described herein, reduced loss of film sensitivity during storage and prior to exposure is obtained.

EXAMPLE 7

Color Photographic Evaluation

Benzothiazolium salts as latent image keeping agents were evaluated in a color negative test. The emulsion used was a 1.6 micrometer equivalent circular diameter, 0.12 micrometer thick tabular emulsion. The emulsion was sulfur and gold sensitized with a yellow optical sensitizing dye. This emulsion was coated in a two layer monochrome with a protective overcoat over the image layer. The image layer contained the emulsion, a yellow dye forming coupler, and the latent image keeping agents coated both at 0.02 and 0.10 mmole/mole Ag. The melt pH was 5.9 and the melt pAg was 7.9. The latent image keeping coatings were exposed for 1/100 seconds and were incubated at 25° C., 50% RH for two and for eight weeks. The check coatings were stored at −18° C. and then were exposed. Both coatings were processed in a C-41 process with Bleach II. The processed coatings were read with status m densitometry. Results are reported in Table 2.

TABLE 2

| Compound | mmole/ Ag mole | Fresh Speed | LIK-check 2 week | 8 week |
|---|---|---|---|---|
| Control | — | 243 | −8 | −13 |
| 11 | 0.02 | 251 | −6 | −12 |
|  | 0.10 | 252 | −6 | −10 |
| 18 | 0.02 | 245 | −6 | −9 |
|  | 0.10 | 243 | −4 | −6 |
| 19 | 0.02 | 245 | −5 | −10 |
|  | 0.10 | 247 | −6 | −9 |

Data in Table 2 show that there is reduced latent image loss in the presence of a benzothiazolium ester containing salt as compared with a control having no agent. Further, these coatings do not suffer loss in sensitivity at the levels that are effective for latent image antihalation.

This invention has been described in detail with particular reference to preferred embodiments thereof, but it will be understood that variations and modifications can be effected within the spirit and scope of the invention.

What is claimed is:

1. A photographic recording material comprising a support and a silver halide emulsion which has associated therewith an N-alkyl or N-alkenylbenzothiazolium or benzoselenazolium salt having the structural formula:

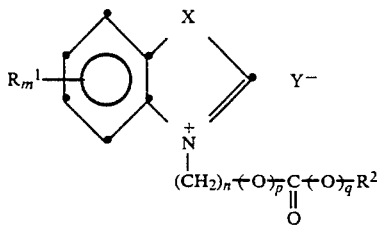

wherein:

X is sulfur or selenium;

$R^1$ is hydrogen, halogen, lower alkyl or lower alkoxy;

$R^2$ is $-CH_2CH_3$ or $-CH=CH_2$;

Y is a counterbalancing ion;

m is 0 to 4;

n is 1 to 5; and p and q are each 0 or 1, with the proviso that when p is 1, q is 0 and when q is 1, p is 0;

2. The recording material of claim 1 wherein X is sulfur.

3. The recording material of claim 2 wherein $R^1$ is hydrogen.

4. The recording material of claim 2 wherein $R^1$ is chlorine.

5. The recording material of claim 2 wherein $R^1$ is alkyl or alkoxy having from 1 to about 5 carbon atoms.

6. The recording material of claim 2 wherein $R^1$ is 1 to 3 carbon atoms.

7. The recording material of claim 2 wherein n is from 1 to 3.

8. The recording material of claim 1 wherein the salt is present in an amount of from 0.002 to about 10 millimoles thereof per mole of silver.

9. The recording material of claim 8 wherein the salt is present in an amount of from 0.02 to about 0.5 millimole thereof per mole of silver.

10. The recording material of claim 1 wherein $R^2$ is $-CH=CH_2$.

11. The recording material of claim 1 which is a color photographic recording material.

12. The recording material of claim 1 wherein the salt has the structural formula:

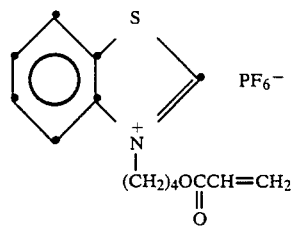

13. The recording material of claim 1 wherein the salt has the structural formula:

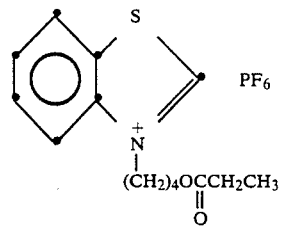

14. The recording material of claim 1 wherein the salt has the structural formula:

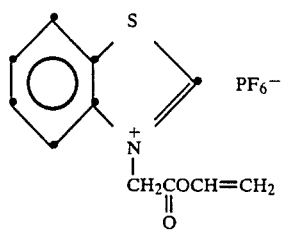

15. The recording material of claim 1 wherein the salt has the structural formula:

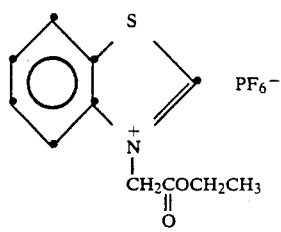

16. The recording material of claim 1 wherein the salt has the structural formula:

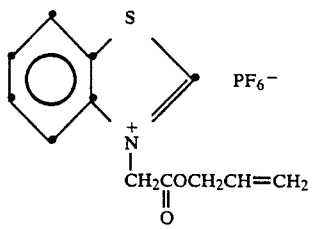

* * * * *